United States Patent [19]

Abramson

[11] 4,152,017
[45] May 1, 1979

[54] SWIVEL CONNECTOR FOR ENDOTRACHEAL TUBE OR THE LIKE

[75] Inventor: Harvey J. Abramson, New York, N.Y.

[73] Assignee: Metatech Corporation, Northbrook, Ill.

[21] Appl. No.: 822,563

[22] Filed: Aug. 8, 1977

[51] Int. Cl.² .................. F16L 31/00; F16L 25/00; A61M 7/02
[52] U.S. Cl. ................ 285/260; 285/DIG. 22; 285/423; 285/280; 128/351
[58] Field of Search ............ 128/351, 348, 349 R, 128/350, DIG. 26, 214, 214.4, 247; 285/DIG. 22, 423, 280, 278, 260

[56] References Cited
U.S. PATENT DOCUMENTS

| 3,827,734 | 8/1974 | Brown | 285/DIG. 22 X |
| 4,009,720 | 3/1977 | Crandall | 128/351 |
| 4,029,105 | 6/1977 | Faust | 128/351 |
| 4,033,353 | 7/1977 | La Rosa | 128/351 |

Primary Examiner—Stephen C. Pellegrino
Attorney, Agent, or Firm—Leydig, Voit, Osann, Mayer & Holt, Ltd.

[57] ABSTRACT

A swivel type junction fitting for an endotracheal tube or the like formed of hollow cylindrical male and female members telescoped together, the female member having at one end a land surface and an adjacent annular groove together with an axially offset centering surface. The male member has at its tip an annular guide surface and a shallow annular ridge offset from the guide surface. The ridge has an interfering fit with respect to the land surface on the female member, and at least one of the members is molded or relatively soft resilient plastic so that when the members are pressed together the ridge clicks past the land surface and into permanent register with the groove with detent action, accompanied by movement of the guide surface into a position opposite the centering surface for relative swiveling of the members free of cocking or binding.

5 Claims, 5 Drawing Figures

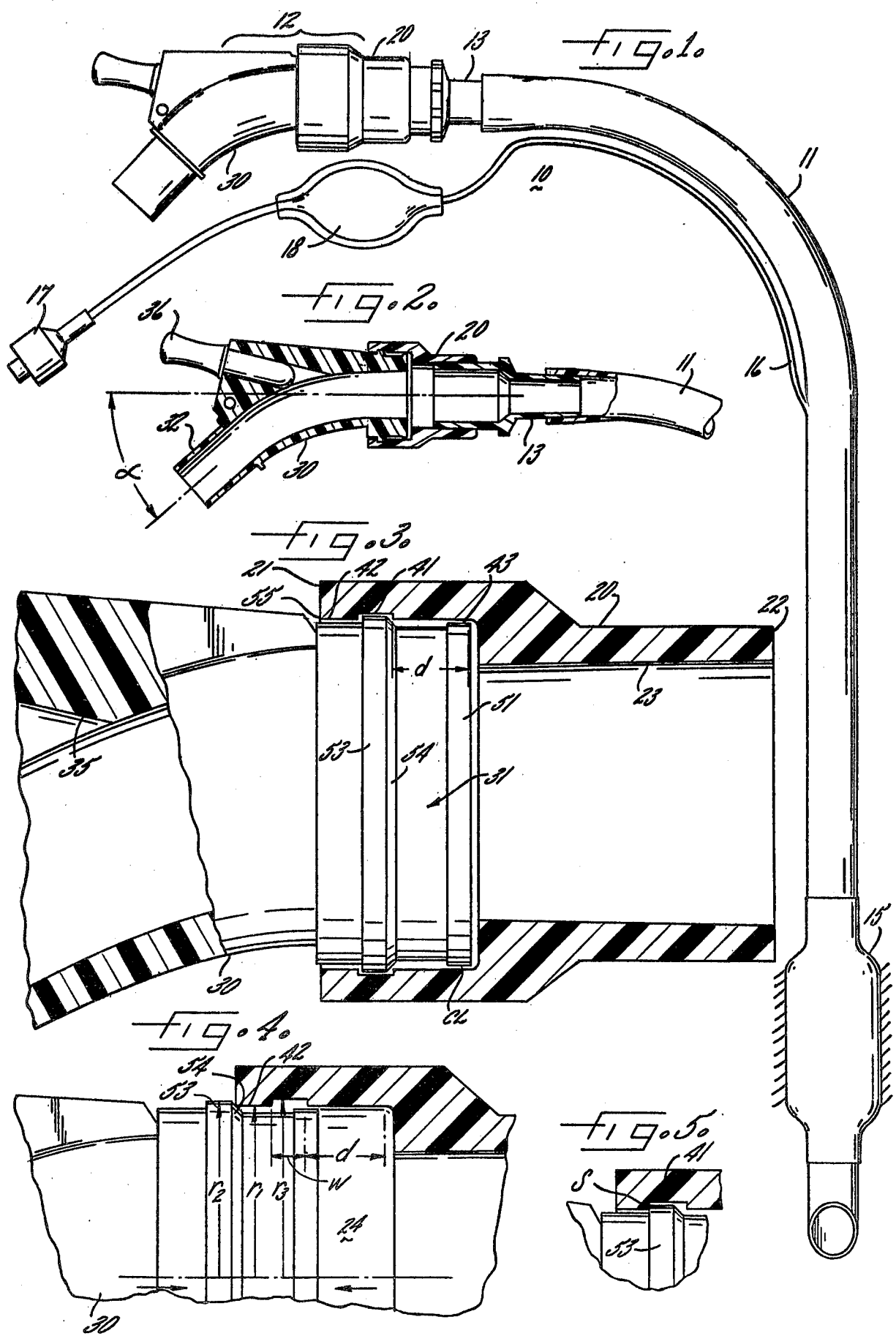

SWIVEL CONNECTOR FOR ENDOTRACHEAL TUBE OR THE LIKE

A typical endotracheal tube assembly is formed of a length of soft tubing which is inserted into the trachea and which is connected, at its upper end, to a junction fitting for the making of a connection to associated equipment. The desirability has been recognized of making the fitting of the swiveling type but such fittings have not been considered satisfactory, being relatively complicated, expensive and unreliable, subject to leakage and prone to cocking and binding.

It is, accordingly, an object of the present invention to provide a swivel type junction fitting for an endotracheal tube or the like permitting lead-off in any direction through 360° with free swiveling action and avoidance of cocking or binding effects. It is a related object to provide a swivel type fluid coupling in which there is a minimum of contact area and hence a minimum of frictional drag. It is another object to provide a swivel type junction fitting which is capable of providing a substantially perfect seal as the result of slight differential pressure. It is yet another object to provide a swivel type fitting which is easily and quickly assembled simply by pressing together, with the assembly being thereafter permanent and tamper-proof. It is finally an object to provide a swivel type junction fitting for an endotracheal tube which is simple in construction, consisting of an interfitting pair of molded parts constructed to normal tolerances. Indeed the fitting may be constructed at a cost which permits single use disposability, but with the assembly nonetheless capable of sterilization and indefinite repeated usage where desired.

Other objects and advantages of the invention will become apparent upon reading the attached detailed description and upon reference to the drawing in which:

FIG. 1 shows, in elevation, an endotracheal tube having a swivel type junction fitting constructed in accordance with the present invention;

FIG. 2 shows the upper portion of the assembly in cross section;

FIG. 3 is an enlarged fragmentary cross section showing the details of the swivel connection;

FIG. 4 is a fragmentary section showing one of the members being forcibly cammed into the other during assembly;

FIG. 5 is a fragment showing the sealing which occurs between the members as a result of slight differential pressure.

While the invention has been described in connection with a preferred embodiment, it will be understood that I do not intend to be limited to the particular embodiment shown but intend, on the contrary, to cover the various alternative and equivalent forms of the invention included within the spirit and scope of the appended claims.

Referring to the drawing, an endotracheal tube assembly indicated at 10 is formed of a length of soft plastic tubing 11 having a junction fitting 12 at its upper end with an interposed tapered nipple 13. For sealing to the inner wall of the trachea, the tube 11 has, at its lower end, an auxiliary inflated "cuff" 15 formed of light gauge latex and which is inflated via a small diameter air line 16, the terminal portion of which is formed integrally with the wall of the tube. The line 16 is coupled to a rudimentary pump through a check valve 17. Preferably included in the line 16 is a small bladder, or tell-tale, 18 which, by its inflated condition, provides constant indication that pressure is being maintained in the cuff.

Turning attention to the junction fitting 12, shown in detail in FIGS. 3 and 5, it will be seen to include a hollow cylindrical female member 20 having respective ends 21, 22 and an inner wall 23. The member is formed at its end with an annular recess 24. Fitted into the recess is a hollow male member 30 having a first end 31 which freely swivels inside the end 21 of the female member and having a secondary end 32 in the form of a taper connection which leads off from the axis of the fitting at an angle $\alpha$ to a source of gas or to other associated apparatus. A port 35 is provided in the member 30 for the purpose of inserting a suction catheter, the port being normally closed by a soft plastic plug 36.

In carrying out the present invention the female member 20 is provided with a shallow annular groove 41 bounded by an annular land surface 42 adjacent the mouth of the recess 24. The female member is further provided with an annular centering surface 43 which is spaced or offset axially inwardly from the groove a distance d which greatly exceeds the width W of the groove. These elements cooperate with corresponding elements on the male member. Thus the male member has, at its tip, an annular guide surface in the form of a slightly upraised bead 51 which cooperates with the centering surface 43. Spaced inwardly on the male member with the same amount of offset d is an annular ridge 53 of shallow height which cooperates with the groove 41. The ridge 53 is narrower than the groove and has a radius $r_2$ (FIG. 5) which is less than the radius $r_3$ of the groove, so that the ridge may be accommodated in the groove. However, the radius $r_2$ is slightly greater than the radius $r_1$ of the adjacent land surface 42 so that there is an interfering fit between the ridge 53 and the land surface which must be overcome, by detent action, when assembling the members together.

Thus, according to one of the features of the present invention, at least one of the members 20, 30 is formed of relatively soft and resilient plastic, and at least one of the members is provided at the region of interference with a one-way cam surface so that the member which is formed of soft plastic may resiliently deform, with the ridge 53 clicking past the land surface 42, with detent action, into permanent register with the groove 41.

In the present instance the camming is accomplished by forming a chamfer 54 at the leading edge of the ridge 53, with the chamfer engaging the sharp corner 55 of the land surface 42. However it will be apparent that this relationship may be reversed, if desired, and the chamfer may be formed on the corner 55, with the chamfer on the ridge then being omitted. Or, as a further alternative, both the ridge 53 and corner 55 may be slightly chamfered. In any event, the effect of forcible assembly, by pressing the members together in the axial direction, is to expand the female member outwardly and to compress the male member inwardly until the ridge 53 snaps over the land surface 42 and into the groove. To facilitate relative deformation of the members during detenting, the female member is made of a plastic such as polyvinylchloride or polyethylene while the male member is formed of a relatively harder plastic such as acrylicbutylstyrene, commonly referred to as ABS.

Making the two members of plastic having unlike characteristics not only facilitates assembly but results, in the case of the most commonly used plastics, in a lower coefficient of friction. This combined with the limited contact, or bearing, areas between the members permits the male member to swivel freely inside of the female member with minimum drag and without requiring grease or other lubrication. Any suitable assembling jig may be employed to force the two members relatively together in the direction of the arrows shown in FIG. 4.

It is one of the features of the present construction that the cocking or binding which tends to limit the freedom of swiveling action in conventional swivel-type fittings is largely precluded in the present construction. Because of the axial spacing d between the ridge at 53 and groove 41 on the one hand and between the guide surface 51 and centering surface 43 on the other hand, the angle of relative off-axis cocking of the members is limited substantially to that which is permitted by the radial clearance CL(FIG. 3); indeed, while the construction provides a high degree of dimensional freedom, the cocking angle is limited to a negligible level. Moreover, freedom of swiveling action is preserved even though two members are subjected to forces in different planes or directions. For example, with the tracheal tubing in place a substantial cantilever loading may be applied by auxiliary apparatus to the outer end of the male member 30, with the only effect being one of self-centering in which the direction of lead-off is rotated into coincidence with the direction of the applied force.

After the tube has been positioned and the cuff 15 is properly inflated, and after all connections have been made so that a slight pressure exists in the tube, it is found that the effect of the slight pressure is to expand the assembly so that the male member 31 moves outwardly to create a seal S as indicated in FIG. 5 between the ridge 53 and the outer ledge of the groove 41. In the event of existence of a relative vacuum within the endotracheal tubing, an equivalent seal will exist between the ridge 53 and the opposite ledge of the groove.

It will be apparent that the device has amply fulfilled the objects set forth above. Swiveling may occur in any direction through an angle of 360° freely and without sacrifice of the seal. The device once detented together is permanently assembled and consequently tamperproof. Perfect reliability is achieved without resort to extremely close tolerances, and the device may be molded and assembled at a cost which is so low as to enable the assembly to be disposable after a single usage; nevertheless, the device is inherently long-lived so that, with appropriate sterilization, it may be used over and over again without degradation of reliability of performance. The device is, moreover, of extremely light weight so that it may be more comfortably worn by the patient than the heavy fittings, usually of metal, commonly used.

I claim:

1. A junction fitting for an endotracheal tube or the like comprising, in combination, a hollow cylindrical female member having a cylindrical recess at one end, a hollow cylindrical male member, having one end dimensioned to swivel freely in the recess in telescoped relation, the male member having an angular lead-off, the female member having a land surface and a shallow annular groove adjacent the mouth of the recess, the female member further having an annular centering surface spaced axially inwardly from the groove at an offset distance which greatly exceeds the width of the groove, the male member having at its tip an annular guide surface and having a shallow annular ridge spaced axially inwardly therefrom by an amount equal to the axial offset in the female member so that when the ridge is alined with the groove the guide surface is opposite the centering surface thereby to preventing cocking of the members with respect to one another, the ridge having an interfering fit with the land surface adjacent the mouth of the recess, at least one of the members being formed of relatively soft resilient plastic capable of deforming accommodation when the members are pressed together, and the ridge being narrower than the groove so that the ridge clicks past the land surface and into register with the groove with detent action is permanently assembled swivelling relation accompanied by movement of the guide surface into position opposite the centering surface.

2. The combination as claimed in claim 1 in which at least one of the land and ridge have a chamfer formed thereon for cammingly guiding the members past the region of interfering fit and into registered relation.

3. The combination as claimed in claim 2 in which the leading edge of the groove is chamfered to provide the cam surface.

4. The combination as claimed in claim 1 in which the guide surface at the tip of the male member is in the form of a shallow radially extending annular bead having a radius which is less than the radius of the annular land surface.

5. The combination as claimed in claim 1 in which the female member is molded of a plastic which is softer and more readily deformable than the plastic of which the male member is made.

* * * * *